United States Patent
Schuren et al.

(10) Patent No.: US 8,403,873 B2
(45) Date of Patent: *Mar. 26, 2013

(54) COMPRESSION BANDAGE SYSTEM

(75) Inventors: Joannes F. H. M. Schuren, Linne (NL);
Eva-Maria Graf, Haan (DE); John J. Rogers, St. Paul, MN (US); Gregory R. Lambach, South St. Paul, MN (US); Robert J. Maki, Hudson, WI (US); Kay Mohr, Sudiohn-Oeding (DE)

(73) Assignee: 3M Innovative Properties Company, Saint Paul, MN (US)

( * ) Notice: Subject to any disclaimer, the term of this patent is extended or adjusted under 35 U.S.C. 154(b) by 228 days.

This patent is subject to a terminal disclaimer.

(21) Appl. No.: 12/945,019

(22) Filed: Nov. 12, 2010

(65) Prior Publication Data
US 2011/0071453 A1    Mar. 24, 2011

Related U.S. Application Data (63) Continuation of application No. 11/397,991, filed on Apr. 5, 2006, now Pat. No. 7,854,716.

(30) Foreign Application Priority Data

Apr. 8, 2005 (EP) ................................ 05007775

(51) Int. Cl.
*A61L 15/00* (2006.01)
*A61F 13/00* (2006.01)
*A61F 15/00* (2006.01)

(52) U.S. Cl. ........................................ 602/75; 602/53

(58) Field of Classification Search ............... 602/41, 602/42, 53, 57, 58, 74–79; 2/22, 62, 255, 2/262, 911
See application file for complete search history.

(56) References Cited

U.S. PATENT DOCUMENTS

| | | |
|---|---|---|
| RE24,906 E | 12/1960 | Ulrich |
| 3,508,544 A | 4/1970 | Moore et al. |
| 3,575,782 A | 4/1971 | Hansen |
| 3,908,645 A | 9/1975 | Sandvig |
| 4,349,020 A * | 9/1982 | Krikorian ........................ 602/75 |
| 4,534,354 A | 8/1985 | Bonner, Jr. et al. |
| 4,699,133 A | 10/1987 | Schafer et al. |
| 4,871,812 A | 10/1989 | Lucast et al. |
| 4,906,240 A | 3/1990 | Reed et al. |
| 4,944,958 A | 7/1990 | Langen et al. |
| 4,984,584 A | 1/1991 | Hansen et al. |
| 5,006,401 A | 4/1991 | Frank |

(Continued)

FOREIGN PATENT DOCUMENTS

| | | |
|---|---|---|
| EP | 0 878 179 A2 | 11/1998 |
| WO | WO 97/42985 | 11/1997 |

(Continued)

OTHER PUBLICATIONS

European Search Report for application No. EP 10174586, dated Apr. 19, 2011.

(Continued)

*Primary Examiner* — Kristen Matter
(74) *Attorney, Agent, or Firm* — Trisha D. Adamson (57) ABSTRACT

A compression bandaging system includes inner and outer bandages. The inner bandage is an inner skin facing, elongated, elastic bandage and includes an elongated, elastic substrate and an elongated foam layer affixed to a face of the substrate. The outer bandage is an outer, elongated, self-adhering elastic bandage having a compressive force when extended. In use, the outer bandage overlies the inner bandage.

14 Claims, 3 Drawing Sheets

U.S. PATENT DOCUMENTS

| | | | |
|---|---|---|---|
| 5,036,838 A | | 8/1991 | Sherman |
| 5,089,606 A | | 2/1992 | Cole et al. |
| 5,098,500 A | | 3/1992 | Reed et al. |
| 5,156,589 A | | 10/1992 | Langen et al. |
| 5,409,472 A | | 4/1995 | Rawlings et al. |
| 5,718,674 A | * | 2/1998 | Penrose .................. 602/46 |
| 5,762,623 A | * | 6/1998 | Murphy et al. ............ 602/75 |
| 5,843,018 A | | 12/1998 | Shesol et al. |
| 5,849,325 A | | 12/1998 | Heinecke et al. |
| 5,939,339 A | * | 8/1999 | Delmore et al. .......... 442/149 |
| 6,143,946 A | | 11/2000 | Docter |
| 6,156,424 A | | 12/2000 | Taylor |
| 6,211,426 B1 | | 4/2001 | Abrams |
| 6,254,554 B1 | | 7/2001 | Turtzo |
| 6,383,630 B1 | | 5/2002 | Jauchen et al. |
| 6,488,643 B1 | | 12/2002 | Tumey et al. |
| 6,548,727 B1 | | 4/2003 | Swenson |
| 6,555,730 B1 | | 4/2003 | Albrod et al. |
| 6,573,419 B2 | | 6/2003 | Naimer |
| 6,663,584 B2 | | 12/2003 | Griesbach et al. |
| 6,759,566 B1 | | 7/2004 | Court et al. |
| 6,958,048 B2 | | 10/2005 | Bonutti |
| 7,014,849 B1 | | 3/2006 | Hunziker et al. |
| 7,135,213 B2 | | 11/2006 | Maki et al. |
| 2002/0099318 A1 | | 7/2002 | Suehr et al. |
| 2003/0040691 A1 | | 2/2003 | Griesbach, III et al. |
| 2004/0002676 A1 | | 1/2004 | Siegwart et al. |
| 2005/0209545 A1 | | 9/2005 | Farrow et al. |
| 2006/0122548 A1 | | 6/2006 | Abrams |
| 2007/0299383 A1 | * | 12/2007 | Murphy et al. ............ 602/46 |
| 2008/0014386 A1 | * | 1/2008 | Murphy et al. ............ 428/34.1 |
| 2008/0014387 A1 | * | 1/2008 | Murphy et al. ............ 428/34.1 |

FOREIGN PATENT DOCUMENTS

| | | |
|---|---|---|
| WO | WO 99/27975 | 6/1999 |
| WO | WO 99/28539 | 6/1999 |
| WO | WO 99/56683 | 11/1999 |

OTHER PUBLICATIONS

European Search Report for application No. EP 10174584, dated Mar. 28, 2011.

European Search Report for application No. EP 10174583, dated Apr. 18, 2011.

Carl, J. C.; "Neoprene Latex—Principles of Compounding and Processing"; 1962; p. 100 (under section entitled Contact Bond Ahesives).

Lohmann Rauscher Brochure entitled: "Support and Relief," Dressing for Compression Therapy, pp. 75-100; *This brochure is believed to be the English equivalent of "Brochure Rosidal® sys Die effective Kompressionstherapie des Ulcus cruis" from Lohmann Rauscher.*

Melhuish, J.M. et al.; "Evaluation of Compression under an Elastic Tubular Bandage Utilised as an Introduction to Compression Therapy in the Treatment of Venous Leg Ulcers"; Phlebology 15 (2000) pp. 53-59.

Rosidal® Brochure "Rosidal® sys Die effective Kompressionstherapie des Ulcus cruis" from Lohmann Rauscher (8 pgs.).

Rosidal® Brochure "Rosidal® sys Die effective Kompressionstherapie des Ulcus cruis" from Lohmann Rauscher (8 pgs.), Date = before Apr. 8, 2005.

Skeist, I.; "Handbook of Adhesives" Third Edition; 1990; p. 305.

Wright, D.D.I. et al.; "The Function of Multiple Layer Compression Bandaging in the Management of Venous Ulcers"; Swiss Med 10 (1988) No. 4a; pp. 109-110.

International Search Report for PCT/US06/13019 dated Apr. 24, 2007.

Complaint for Patent Infringement in *3M Company and 3M Innovative Properties Company v. Andover Healthcare, Inc.* filed in U.S. District Court of Minnesota on Dec. 21, 2010.

Answer of Andover Healthcare, Inc. (Jury Trial Demanded) in *3M Company and 3M Innovative Properties Company v. Andover Healthcare, Inc.* filed in U.S. District Court of Minnesota on Feb. 15, 2011.

* cited by examiner

Fig. 4

COMPRESSION BANDAGE SYSTEM

CROSS REFERENCE TO RELATED APPLICATIONS

This application is a continuation of U.S. Ser. No. 11/397,991, filed Apr. 5, 2006, now U.S. Pat. No. 7,854,716, which claims priority to European Patent Application No. 05007775.9, filed Apr. 8, 2005, the disclosures of which are incorporated by reference herein.

BACKGROUND

This invention relates to compression bandage systems, in particular for the use in the treatment and/or management of venous leg ulceration.

Compression bandages are known for use in the treatment of oedema and other venous and lymphatic disorders, e.g., of the lower limbs. An area where compression bandages are considered particularly useful is in the management and treatment of chronic wounds, such as venous leg ulcers.

The mainstay in nearly all venous leg ulcer treatments is the application of a 3 to 4 layer compression bandage, whereby the concept of such multi-layer bandaging is the use of a combination of different types of bandage layers in order to apply pressure in layers (giving an accumulation of pressure) and to provide sustained compression together with rigidity. A common, widely used bandage is a four-layer system including an inner layer of absorbent orthopedic wool, a second layer crepe bandage, a third layer of light compression bandage and a fourth layer of self-adherent (cohesive) flexible bandage. Such a bandaging system has been described in "The Function of Multiple Layer Compression Bandaging in the Management of Venous Ulcers," DDI Wright et al, SWM, 10, 109.10, 1988, and is, e.g., commercially available under the trade designation "PROFORE". Although such 3 to 4 layer bandaging systems provide sufficient pressure for therapeutic treatment and/or management of chronic wounds such as venous leg ulcers, the process of applying such bandages, however, is difficult (for example to obtain the desired pressure and/or a relatively uniform pressure) as well as time consuming. Also such bandages are prone to slipping and/or forming wrinkles after being applied which may result in insufficient and/or uneven compression being applied and/or cause discomfort to the patient.

Although other compression bandage systems (such as those disclosed in U.S. Pat. No. 6,759,566 and US 2002/0099318) have been proposed in attempts to provide bandaging systems that are easier to apply, in particular by inexperienced staff, such systems often do not provide the desired therapeutic compressive pressure or are not capable of maintaining the desired therapeutic compressive pressure for extended periods of time. Furthermore, such systems typically still have a tendency (and in some cases an increased tendency) to slip and/or wrinkle after application.

SUMMARY OF THE INVENTION

A compression bandaging system includes inner and outer bandages. The inner bandage is an inner skin facing, elongated, elastic bandage and includes an elongated, elastic substrate and an elongated foam layer affixed to a face of the substrate. The elongated foam layer extends 33% or more across the face of the substrate in transverse direction, and 67% or more across the face of the substrate in longitudinal direction. The outer bandage is an outer, elongated, self-adhering elastic bandage having a compressive force when extended.

The compression bandaging system can be used to provide desired therapeutic effect for extended periods of time. The compression bandaging system can be used such that the inner bandage faces the skin and the outer bandage overlies the inner bandage. The inner skin facing, elongated, elastic bandage can adhere to the outer, elongated, self-adhering elastic bandage. In use, the inner skin facing, elongated, elastic bandage can adhere to the outer, elongated, self-adhering elastic bandage under elastic extension without the use of a fastening mechanism. In some embodiments, the system is free of any additional elongated bandages.

The inner bandage can comprise an outer face not affixed to the foam layer, wherein the exposed face comprises a self-adhering material such as a self-adhering elastomeric material. The compression bandage system can be designed such that the inner skin facing, elongated, elastic bandage provides less compression than the outer, elongated, self-adhering elastic bandage when extended. The elongated foam layer can be coextensive with the elongated, elastic substrate. The compression bandage system can further comprise a non-elongated wound dressing or plaster. The outer bandage can have a stretch capability of 75% at most in the longitudinal direction, and/or a recovery-of-stretch capability of at least 85% in the longitudinal direction. The inner bandage can have a stretch capability of less than 75% in the longitudinal direction, and/or a recovery-of-stretch capability of at least 80% in the longitudinal direction. The foam layer can have a thickness greater than 1.6 mm.

Surprisingly, it has been found that through the provision of a compression bandaging system comprising: (a) an inner skin-facing, elongated, elastic bandage comprising an elongated, elastic substrate and an elongated layer of foam, said foam layer being affixed to a face of the substrate and extending 33% or more across the face of substrate in transverse direction and 67% or more in longitudinal direction; and (b) an outer, elongated, self-adhering elastic bandage which has a compressive force when extended, it is possible to provide a compression bandage system which is easy to apply and provides desired therapeutic effect for extended periods of time.

In some embodiments, in use, the compression bandaging system comprises: a) an inner skin facing, elongated, elastic bandage having inner and outer faces and comprising: (i) an elongated, elastic substrate having first and second faces, the second face comprising a self-adhering material, and (ii) an elongated layer of foam, said foam layer being affixed to the first face of said substrate and extending 33% or more across said first face of substrate in transverse direction and 67% or more across said first face of substrate in longitudinal direction, the foam layer having an exposed face not affixed to the first face of said substrate and not comprising a self-adhering material, the inner face of the inner bandage comprising the exposed face of the foam layer, and the outer face of the inner bandage comprising the second face of the elongated, elastic substrate; and b) an outer, elongated, self-adhering elastic bandage; said bandage having a compressive force when extended; wherein, in use, said outer bandage overlies the inner bandage, and said inner face of the inner bandage faces the skin, and the outer face of the inner bandage faces said outer bandage, wherein the inner and outer bandages are configured and adapted such that in use said bandages remain adhered to one another under elastic extension without the use of a fastening mechanism, and wherein the bandaging system is free of any additional elongated bandages.

In some embodiments, in use, the compression bandaging system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage, wherein the inner and outer bandages are configured and adapted such that in use said bandages remain adhered to one another under elastic extension without the use of a fastening mechanism, wherein the bandaging system is free of any additional elongated bandages, and wherein the elongated, elastic substrate of the inner bandage, when extended, provides less compression than the outer bandage when extended.

In some embodiments, in use, the compression bandaging system comprises: a) an inner skin facing, elongated, elastic bandage having inner and outer faces and comprising: (i) an elongated, elastic substrate having first and second faces, the second face comprising a self-adhering material, and (ii) an elongated layer of foam, said foam layer being affixed to the first face of said substrate and extending 33% or more across said first face of substrate in transverse direction and 67% or more across said first face of substrate in longitudinal direction, the foam layer having an exposed face not affixed to the first face of said substrate and not comprising a self-adhering material, the inner face of the inner bandage comprising the exposed face of the foam layer, and the outer face of the inner bandage comprising the second face of the elongated, elastic substrate; and b) an outer, elongated, self-adhering elastic bandage; said bandage having a compressive force when extended; wherein, in use, said outer bandage overlies the inner bandage, and said inner face of the inner bandage faces the skin, and the outer face of the inner bandage faces said outer bandage, wherein the inner and outer bandages are configured and adapted such that in use said bandages remain adhered to one another under elastic extension without the use of a fastening mechanism, and wherein the bandaging system is free of any additional elongated bandages, and the inner bandage when extended provides less compression than the outer bandage when extended.

The term "elongated bandage" as used herein is generally understood to mean that the bandage is sufficiently elongated so as to be capable of being wound 2 turns or more (more suitably 5 turns or more) about a limb of a patient.

In use, the foam layer of the inner bandage faces the skin with the outer bandage overlaying the inner bandage. It has been found that due to the elasticity of the inner bandage substrate as well as advantageous interfacing between it and the outer bandage upon application, the skin-facing foam layer, in particular the exposed face of the foam layer facing directly towards the skin of the patient, demonstrates a particularly desirable and effective fastening onto the skin of the patient, which minimizes of tendency of the bandage system towards slippage after application.

It has been found preferable to provide an outer, elastic, compression bandage having a stretch capability in the longitudinal direction of not more than 75% (more preferably not more than 65%, most preferably not more than 55%). With such outer compression bandages, it is relatively easy, in particular for inexperienced staff, to apply the bandage at the desired therapeutic pressure, for example by applying the outer bandage at or close to full extension. Furthermore, it was found that the use of outer bandages having such limited extensibility aids in providing desirably low resting pressures and yet at the same time high walking pressures of the applied bandage system.

For yet further ease in application and avoidance of formation of wrinkling of the inner skin facing bandage during application of the bandage, it has been found preferably to provide an inner bandage having a stretch capability of less than 75% (more preferably less than 65%, most preferably less than 50%) in the longitudinal direction.

It also has been found particularly advantageous to configure and adapt the outer bandage and the inner bandage, such that in use the inner and outer bandages remain adhered to one another under elastic extension, e.g., without the use of a fastening mechanism. With such preferred embodiments, after application, the outer and inner bandages in principle act as a single bandaging entity—minimizing, if not eliminating, any potential of slippage and/or wrinkling between the two bandaging layers, and thus facilitating comfort for the patient as well as overall conformability of the complete, applied bandaging system and uniformity of compressive pressure over extended periods of time.

Advantageously, bandaging systems described herein allow the provision of effective and sustained therapeutic performance without application of any additional elongated bandages besides the herein described inner and outer bandages.

As mentioned above, in use of bandaging systems described herein, the exposed face 14 of the foam layer 12 facing directly towards and coming into the contact with the skin of the patient demonstrates a particularly desirable and effective fastening onto the skin of the patient, which facilitates the minimization of tendencies of the bandage system towards slippage after application. To allow for desirable contouring of the foam layer to the particular limb of the patient and thus further enhanced, advantageous fastening of the foam onto the skin, the foam preferably has a thickness greater than 1.6 mm, more preferably greater than 2 mm. Within this range, a thickness of 10 mm or less is suitable; 8 mm or less being more suitable, 6 mm or less even more suitable, 5 mm or less yet even more suitable, 4 mm or less most suitable. To ensure such desirable fastening, the outer, exposed face 14 of the foam layer 12 is typically substantially free of materials, e.g., which could interfere with the foam-skin interface, being affixed to said face of the foam layer, such as fibers, nettings, and anti-adherent films. In some embodiments, the outer, exposed face 14 of the foam layer 12 (the face not affixed to substrate 16) does not comprise a self-adhering material. In other words, the outer, exposed face 14 of the foam layer 12 typically forms the innermost skin-facing surface of the inner bandage, with the possible exception of any optional tab material (typically having a width of 10% or less in the longitudinal direction of the bandage) at one or both terminal transverse ends of the bandage.

Bandaging systems described herein may optionally include a wound dressing or plaster for covering and thus protecting an open wound, such as an ulcer, under the applied bandaging system. Such dressings or plasters are typically appropriately sized to offer protection for the wound and immediate-surrounding skin about the wound. Such wound dressings or plaster are typically non-elongated. The term "non-elongated dressing or plaster" as used herein is generally understood to mean that the dressing or plaster is not sufficiently elongated so as to be capable of being wound two turns about a limb of a patient. Preferably a non-elongated dressing or plaster is sized such that it can only be wound at most one turn about a limb of a patient, more preferably sized such it cannot be wound one turn about a limb of a patient.

Bandaging systems described herein are advantageously provided in the form of a kit-of-parts.

Bandaging systems described herein are particularly adapted for use in the treatment and/or management of oedema and other venous and lymphatic disorders of a limb, more particularly venous leg ulcers and lymphoedema of a limb.

In methods of using compression bandaging systems described herein, the inner bandage is applied, e.g., by spirally winding the bandage about a limb of a patient, with the foam layer facing the skin of the patient, and subsequently the outer bandage is applied, e.g., again by spirally winding the bandage, over the inner bandage. If desired or needed, prior to the application of the inner bandage, a wound dressing or plaster may be applied to a wound or wounds.

The dependent claims define further embodiments of the invention.

It is to be understood that the present invention covers all combinations of particular, suitable, desirable, favorable advantageous and preferred aspects of the invention described herein.

DETAILED DESCRIPTION

Compression bandaging systems in accordance with the present invention include an inner skin facing, elongated, elastic bandage 10 (as exemplified in FIG. 1 and described in detail below) and an outer, elongated, self-adhering, elastic compression bandage 20 (as exemplified in FIG. 2 and described in detail below). Each bandage is sufficiently elongated so as to be capable of being wound 2 or more turns (more suitably 5 or more turns) about a limb of a patient, as exemplified in FIG. 3. The particular, appropriate dimensions of the bandages depend in part on the particular limb being treated and/or the particular patient. For example, in human (adult) therapy for use with lower limbs, suitable dimensions for the bandages may be about 70 to about 130 mm wide and about 2 to about 4.5 m long, while for use with upper limbs a width of about 70 to about 130 mm is suitable with a corresponding shorter length than that use for lower limbs. For applications in veterinary medicine, depending on the particular animal patient, appropriate, suitable dimensions may be larger (e.g., for equine bandaging) or smaller (e.g., for canine bandaging).

Each bandage is desirably, sufficiently porous to allow for transmission of air and moisture vapor through the bandage (e.g., a water vapor transmission rate (WVTR) of at least 240 g/m$^2$/24 h, more suitably of at least 400 g/m$^2$/24 h, e.g., as determined by ASTM E398-03 at 37.8° C. and 100% relative humidity in the wet chamber and 37.8° C. and 10% relative humidity in the dry chamber). In addition, each bandage, in particular the inner skin-facing bandage, may be sterilized, e.g., gamma sterilized.

Figure 2:
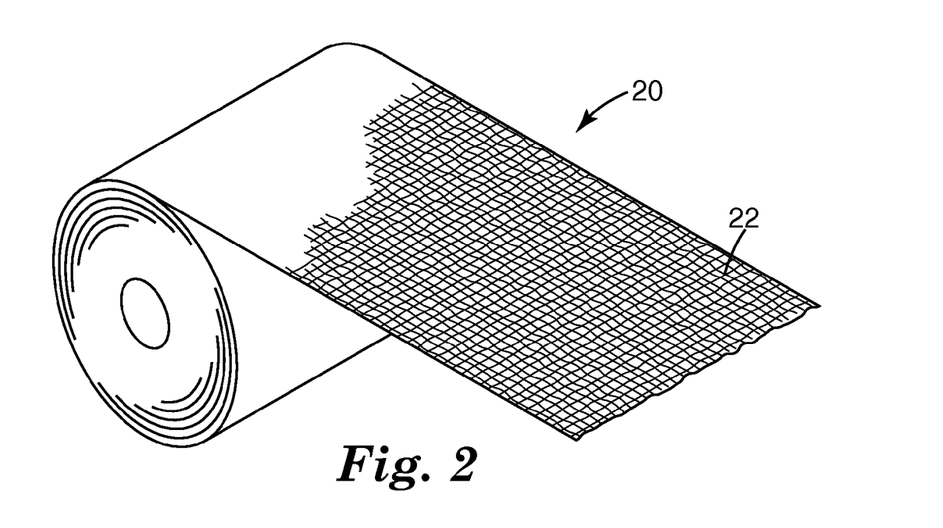
FIG. 2 illustrates an exemplary embodiment of the outer elastomeric bandage.

Referring to FIG. 2, the outer, elongated, self-adhering elastic bandage 20 of compression bandaging systems described herein is adapted to provide a compressive force, more particularly a permanent compressive force, when extended. In use, preferred outer bandages will provide a sub-bandage, resting compressive force of from about 1 to about 80 mm Hg (more suitably from about 20 to about 75 mmHg, most suitably from about 30 to about 70 mmHg) at a position 8 cm above the medial malleolus, when wrapped about a human adult leg with an ankle circumference of 22 cm. A suitable method to measure compressive force is described below in the test protocol—Sub-bandage Pressure Measurement Procedure—which is based on the method reported in Melhuish et al, Phlebology, 15: 53-59 (2000).

As mentioned above, for ease in application and aiding in providing desirable low resting pressures and high walking pressures, it has been found particularly advantageous to provide outer elastic, compression bandages having a limited, relatively low extensibility in its longitudinal direction, in particular having a stretch capability in the longitudinal direction of not more than 75%, more preferably not more than 65%, most preferably not more than 55%, e.g., as determined in accordance with the Stretch Testing Procedure summarized below. Within this range a minimal stretch capability of at least 20% in the longitudinal direction is desirable, at least 25% more desirable, and at least 30% most desirable. To ensure favorable conformability and retention of compressive recovery of the bandage through the time period the bandage is in place, the outer bandage desirably shows high elasticity in its longitudinal direction, in particular a recovery-of-stretch capability of at least 85%, more desirably at least 90%, most desirably at least 95%, in the longitudinal direction, e.g., as determined in accordance with the Stretch Testing Procedure summarized below.

Preferred outer bandages do not adhere to clothing, hair or skin.

Preferred outer bandages are self-adhering elastomeric bandages, more preferably self-adherent elastomeric bandages, which do not adhere to clothing, hair or skin.

Examples of suitable types of self-adherent elastomeric bandages as well as methods of making such bandages are disclosed in U.S. Pat. Nos. 3,575,782; 4,984,584; and US Application 2005/0025937A, the contents of which are incorporated in their entirety herein by reference. Examples of other suitable types of self-adherent elastomeric bandages are disclosed in U.S. Pat. No. 6,156,424, the content of which is incorporated in its entirety herein by reference. Other example of suitable types of self-adherent bandages include knitted and woven bandages commercially available under the trade designations ROSIDAL HAFT (Lohman & Rauscher GmbH & Co. KG, Neuwied Germany) and ACTICO (Activa Health Care, Burton-upon-Trent, UK).

As shown in FIG. 2, outer bandages 20 may suitably comprise a woven, knitted or nonwoven bandage comprising generally a plurality of generally longitudinally extending elastic yarns in the woven, knitted or nonwoven structure 22, said bandage being coated or impregnated with a polymer binder. More suitably outer bandages may comprise a plurality of generally longitudinally extending, (preferably partially extended) elastic yarns bound with a polymeric binder between two webs or bound with a polymeric binder on a web. Favorably the polymeric binder is cohesive, so that the bandage is self-adherent (i.e. in use the bandage will remain adhered to itself under elastic extension e.g., without the use of a fastening mechanism), but will not adhere to clothing, hair or skin. Accordingly, generally the top and bottom faces of the bandage comprise polymeric binder, e.g., where the polymeric binder generally extends throughout the thickness of the bandage.

Suitable polymeric binders providing cohesive properties may be either elastomeric or non-elastomeric polymeric binders, however, preferably the polymeric binder is an elastomeric polymeric binder due to generally favorable properties of such binders, such as long-term flexibility, extensibility and/or elasticity. Suitable elastomeric polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. Examples of suitable polymeric elastomeric binders are disclosed for example in U.S. Pat. Nos. 3,575,782; 4,984,585; and 6,156,424 as well as in textbooks, such as Neoprene Latex: Principles of Compounding and Processing, J. C. Carl, 1962, Delaware, E. I: DuPont de Nemours (e.g., under the section entitled Contact Bond Adhesives, on page 100) and Handbook of Adhesives $3^{rd}$ Edition, Ed. I. Skeist, 1990, New York, Van Nostrand Reinhold (e.g., page 305). Outer bandages may be desirably free of natural rubber latex.

For configurations including elastic yarns bound on a web or between webs, suitable webs include woven, knitted, warp-knit, or nonwoven fibrous webs, woven and nonwoven fibrous webs being more suitable, and nonwoven fibrous webs most suitable in terms of providing a favorably thin outer compression bandage, especially in its extended state. As mentioned above, preferably elastic yarns are partially extended (e.g., being maintained under partial tension) within the bandage. In order to provide preferred limited extensibility in the longitudinal direction as described above, during the manufacturing of such bandages (e.g., during binding of elastic yarns with polymeric binder between said webs or on a web) it is preferable to stretch the yarns to a length of at most 2.0, more preferably at most 1.75, even more preferable at most 1.5, most preferably about 1.5 times their fully relaxed length. The ratio of stretched length to relaxed length of yarn is referred to as draw ratio. Generally a draw ratio of at least 1.2 to 1 is desirable. Extent of compression provided is generally related to, inter alia, size of the elastic yarns and the number of yarns, whereby increased compression is typically a result of using greater number of larger elastic yarns in the bandage. Suitably, the number of elastic yarns per inch (epi) may range from about 8 to about 25 epi, while the elastic yarns may have a denier ranging from about 280 to about 1700. For use in bandaging systems for treatment and/or management of venous leg ulceration, it has been found that the use of from about 10 to about 20 epi together with a elastic yarn denier of about 650 or less (more favorably about 620 or less, most favorably about 580 or less) in outer bandages is beneficial in providing desirable ease in handling of the outer bandage itself as well as desired therapeutic compressive force without observation of undesirable high resting pressures. Within the mentioned denier range, a suitable minimal denier for effective desired therapeutic compressive force may be at least about 350 denier (more favorably at least about 425 denier, and most favorably at least about 500 denier).

Figure 1:
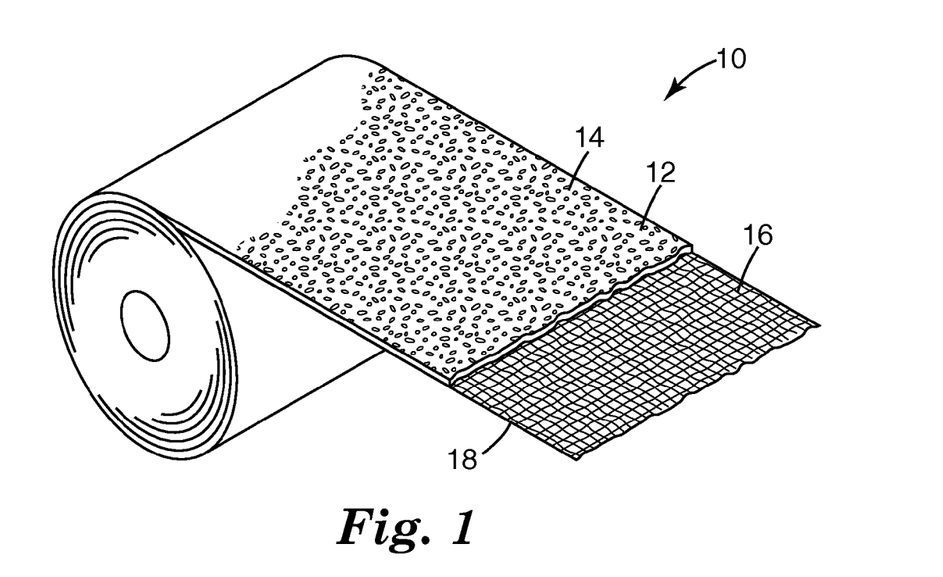
FIG. 1 illustrates an exemplary embodiment of the inner skin-facing bandage.

As shown in FIG. 1, the inner, skin facing elongated, elastic bandage 10 of compression bandaging systems described herein comprises an elongated, elastic substrate 16 and an elongated layer of foam 12, said foam layer 12 being affixed to a face of said substrate 16 and extending 33% or more across the face of substrate 16 in transverse direction and 67% or more across the face of substrate 16 in longitudinal direction.

As mentioned above, for enhanced ease in application and avoidance of formation of wrinkling of the inner skin facing bandage during application of the bandage, it has been found preferably to provide an inner bandage having a stretch capability of less than 75% (more preferably less than 65%, most preferably less than 50%) in the longitudinal direction, e.g., as determined in accordance with the Stretch Testing Procedure summarized below. Within this range a minimal stretch capability of at least 15% in the longitudinal direction is desirable, at least 20% more desirable, and at least 25% most desirable. To ensure favorable conformability, the inner bandage desirably shows a recovery-of-stretch capability of at least 80%, more desirably at least 85%, most desirably at least 90%, in the longitudinal direction, e.g., as determined in accordance with the Stretch Testing Procedure summarized below.

Also as mentioned above, it also has been found particularly advantageous to configure and adapt the outer bandage and the inner bandage (in particular at least the outer face of the inner bandage (e.g., the face of the inner bandage facing away from the skin and towards the outer bandage in use)), such that in use the inner and outer bandages remain adhered to one another under elastic extension, e.g., without the use of a fastening mechanism. Such configurations may include an inner bandage, in particular its outer face, comprising the same self-adherent material as the outer bandage or another appropriate self-adherent material, such that in use the inner and outer bandages remained adhered to one another under elastic extension, e.g., without the use a fastening mechanism.

Desirably the outer face of the inner bandage comprises a self-adhering material, more desirably a self-adhering elastomeric material. The outer face of the inner bandage may be provided with such a self-adherent material, for example by providing (e.g., affixing) an elongated layer or a web including such material onto the second face 18 of the elastic substrate, i.e. the face of the elastic substrate opposite of the face (i.e. the first face) to which the foam layer is affixed. However in consideration of the provision of favorably thin inner bandages and thus wearing comfort for the patient, preferably the second face 18 of the elastic substrate 16 forms the outer face of the inner bandage as shown in FIG. 1. Accordingly, preferred embodiments of the inner bandage comprise an elastic substrate, in particular an elastic substrate in which at least its second face 18, comprises a self-adhering material, more preferably a self-adhering elastomeric material.

The elastic substrate may favorably be made of a material (more favorably a self-adhering material, more favorably a self-adhering elastomeric material), which is capable of exerting a compressive force (in particular a permanent compressive force) when extended. In such preferred embodiments, although the elastic substrate may suitably be made of the same material as the outer bandage, it has been found more suitable to provide a related compression material that it provides a lesser amount of compression (than the outer bandage) when extended.

Elastic substrates may suitably comprise a woven, knitted or a nonwoven web comprising generally a plurality of generally longitudinally extending elastic yarns in the woven, knitted or nonwoven structure, said web being coated or impregnated with a polymer binder. More suitably elastic substrates of the inner bandage may comprise a plurality of generally longitudinally extending, partially extended or non-extended elastic yarns bound with a polymeric binder between two webs or bound with a polymeric binder on a web. Favorably the polymeric binder is cohesive, so that elastic substrate is self-adherent, but will not adhere so clothing, hair or skin. Accordingly, at least the second face and more suitably both faces of the elastic substrate comprise polymeric binder (e.g., where the polymeric binder extends throughout the thickness of the web). Suitable polymeric binders include those described above in connection with outer bandages. Accordingly suitable polymeric binders providing cohesive properties may be either elastomeric or non-elastomeric polymeric binders. Preferably the polymeric binder is an elastomeric polymeric binder. Suitable elastomeric polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. Again examples of suitable polymeric elastomeric binders are disclosed for example in U.S. Pat. Nos. 3,575,782; 4,984,585; and 6,156,424 and in textbooks, such as those mentioned above Inner bandages may be desirably free of natural rubber latex.

In embodiments of the inner bandage, in particular the elastic substrate thereof, including any type of self-adhering material (as described above), it is preferred that the respective self-adhering material does not adhere to clothing, hair or skin.

For configurations including elastic yarns bound on a web or between webs, suitable webs include woven, knitted, warp-knit, or nonwoven fibrous webs, woven and nonwoven fibrous webs being more suitable, and nonwoven fibrous webs most suitable in terms of providing a favorably thin elastic substrate, especially in its extended state. Partially extended yarns are preferred. During the manufacturing of such elastic substrates (e.g., during binding of elastic yarns with polymeric binder between said webs or on a web) it is preferable to stretch the yarns to a length of 5 times or less (more favorably 3.5 or less) times their fully relaxed length. Generally a draw ratio of at least 1.2 to 1 is desirable. Favorably the epi is less than 15, more favorably 12 or less, most favorably 10 epi or less. Within this range, an epi of 4 or more is suitable, 5 or more is more suitable, 6 or more is most suitable. Desirably elastic yarns have a denier less than 550, more desirably 450 or less, most desirably about 350 or less. Within this range, a denier of 100 or more is suitable, 150 or more is more suitable, and 200 or more is most suitable.

As shown in FIG. 1, the foam layer 12 is affixed to the first face of the elastic substrate. A variety of means are suitable for affixing the foam layer 12 onto the elastic substrate 16 such as stitching, needle tacking, ultrasonic welding or bonding, e.g., mechanical, thermal, and chemical bonding as well as combinations thereof. Suitable means of chemical bonding include using an adhesive, for example in the form of a continuous or discontinuous layer (e.g., a pattern-coated adhesive layer). Suitable adhesives for use can be any of those useful for wound dressings, such as those disclosed in WO 99/27975; WO 99/28539; U.S. Re. 24,906; U.S. Pat. No. 5,849,325; and U.S. Pat. No. 4,871,812; the contents of which are incorporated in their entirety herein by reference. Another suitable means of bonding includes providing the first face of the elastic substrate with a polymeric binder, in particular an elastomeric polymer binder, having cohesive properties (as described above) and affixing the foam to the first face of the elastic substrate by applying the foam under pressure onto the substrate (e.g., passing the elongated foam and substrate through two driven rollers at a pressure around 0.3 M Pa), wherein a chemical and/or mechanical bond is provided between the foam and substrate. Alternatively the foam layer 12 may be affixed to the first face of the elastic substrate 16 by forming the foam directly onto the elastic substrate 16. To ensure a relatively smooth, generally non-wrinkled and/or non-puckered foam layer, preferably the foam layer is affixed to the elastic substrate, while the substrate is in a generally non-extended (e.g., 10% or less of the substrate total extensibility) state or a completely relaxed state.

Generally the foam layer 12 is suitably affixed to the elastic substrate 16 beginning substantially at one transverse end of the substrate and extending 67% or more (more desirably 80% or more, more desirably 90% or more, even more desirably 95%) across the length of substrate towards the second transverse end. The portion near the second transverse end of the elastic substrate may be not covered by the foam layer, for example, to provide a tab of elastic substrate alone at the very end of the bandage to allow one or two wraps of elastic substrate onto itself. However in preferred embodiments, as shown in FIG. 1, the foam layer 12 is essentially coextensive or coextensive with the elastic substrate 16 face in the longitudinal direction. That the foam layer is essentially coextensive or coextensive in the longitudinal direction is preferred, because during bandaging it is desired for therapeutic reasons and/or patient comfort to have the person applying the bandage to simply cut off any excess bandage in length, and it has been observed that if the bandage includes a tab at the end, very often the applier, feeling obliged to make use of the tab, will not cut off any excess length.

Also generally the foam layer 12 is suitably affixed to the elastic substrate 16 beginning substantially at one longitudinal edge of the substrate and extending 33% or more across the width of the substrate towards the second longitudinal end. The particular amount of extension of the foam layer 12 across the width of the elastic substrate 16 (transverse extension) depends in part on how the inner bandage is applied. For example applications using a spiral winding of the inner bandage about a limb using standard 67% or 50% overlaps, a 33% and 50% transverse extension, respectively, may be suitable. Here for example as the bandage is spirally wound about the limb, the exposed face 14 of foam layer 12 comes into contact with the skin and the portion of the first inner face (along the length) of elastic substrate, which is not covered by the foam layer, comes into contact with the outer face of the inner bandage (from the previous turn). To further enhance ease in application and more importantly to facilitate uniformity of compressive force upon application of the bandage-system and the maintenance of a uniform compressive force over time after application, it has been found advantageous to apply the inner bandage with an overlap of less than 50% (in particular with an overlap of 33% or less, more particular 20% or less, even more particular 10% or less, most particularly 5% or less). Accordingly the transverse extension of the foam layer is advantageously 50% or more (in particular 67% or more, more particular 80% or more, even more particular 90% or more, yet even more particular 95% or more). In preferred embodiments as shown in FIG. 1, the foam layer 12 is essentially coextensive or coextensive with the first face of the elastic substrate in the transverse direction.

As used herein, the term "foam" refers to a polymeric material containing open and/or closed cells dispersed throughout its mass, preferably polymeric foam containing open cells. Suitable foams for the foam layer include flexible, resilient foams. Suitable foams include, but are not limited to, polyurethane, carboxylated butadiene-sytrene rubber, polyester, polyacrylate, polyether, and polyolefin foams, for example, such as those described in U.S. Pat. Nos. 3,908,645 and 6,548,727, the contents of which are incorporated in their entirety herein by reference. Preferred foam materials are polyurethanes.

For certain therapeutic uses of compression bandaging systems, it may be desirable that said systems, in particular foam layers thereof, absorb wound exudates. Thus foams used for the foam layers may advantageously be absorbent foams, e.g., absorbing greater than 250% aqueous saline solution when immersed for 30 minutes in phosphate saline containing 0.9 wt % NaCl at 37° C., e.g., in accordance with the Saline Absorbency Test outlined below. Suitable open cell foams that allow transport of fluid and cellular debris into and within the foam, generally and desirably have an average cell size (typically, the longest dimension of a cell, such as the diameter) of at least about 30 microns, more desirably at least about 50 microns, and desirably no greater than about 800 microns, more desirably no greater than about 500 microns, as measured by scanning electron microscopy (SEM) or light microscopy. Favorably to aid in preventing skin macerations, such foams may also be desirably, substantially non-swelling, e.g., increasing in volume by no greater than about 15% following a 30-minute soaking in phosphate saline containing 0.9 wt % NaCl at 37° C., e.g., in accordance with the Saline Swelling Test outlined below. However surprisingly it has been observed that for foams showing higher swelling characteristics, e.g., greater than 15% (in particular up to 75%, more particular up to 55% and most particular up to 35%) in accordance with the Saline Swelling Test, during use in the compression of the foam layer, such foam of the foam layer typically does not show any significant swelling or only a minimal amount of swelling due to compression forces of the bandaging system pushing and distributing absorbed fluid and cellular debris throughout the foam layer. This also holds true for foam layers made of substantially non-swelling foams.

Suitable foams may be either hydrophilic or hydrophobic, more suitably they may be hydrophobic and treated to render them more hydrophilic, e.g., with surfactants such as non-ionic surfactants, such as oxypropylene-oxyethylene block copolymers.

As mentioned above, in use of bandaging systems described herein, the exposed face 14 of the foam layer 12 facing directly towards and coming into the contact with the skin of the patient demonstrates a particularly desirable and effective fastening onto the skin of the patient, which facilitates the minimization of tendencies of the bandage system towards slippage after application. To allow for desirable contouring of the foam layer to the particular limb of the patient and thus further enhanced, advantageous fastening of the foam onto the skin, the foam preferably has a thickness greater than 1.6 mm, more preferably greater than 2 mm. Within this range, a thickness of 10 mm or less is suitable; 8 mm or less being more suitable, 6 mm or less even more suitable, 5 mm or less yet even more suitable, 4 mm or less most suitable. To ensure such desirable fastening, the outer, exposed face 14 of the foam layer 12 is typically substantially free of materials, e.g., which could interfere with the foam-skin interface, being affixed to said face of the foam layer, such as fibers, nettings, and anti-adherent films. In other words, the outer, exposed face 14 of the foam layer 12 typically forms the innermost skin-facing surface of the inner bandage, with the possible exception of any optional tab material (typically having a width of 10% or less in the longitudinal direction of the bandage) at one or both terminal transverse ends of the bandage.

Figure 3A:
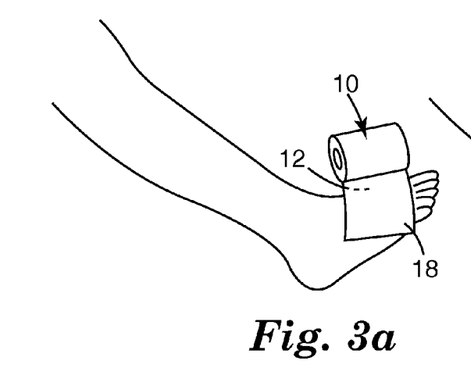
FIGS. 3a-3e and 4 illustrate exemplary embodiments of using the compression bandaging system.
Figure 3B:
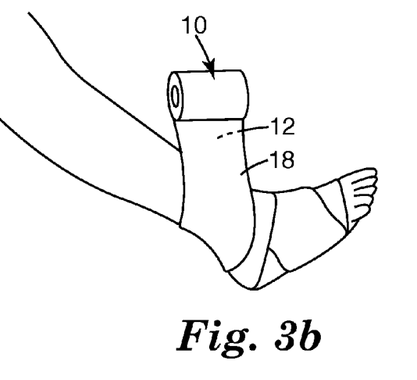
Figure 3C:
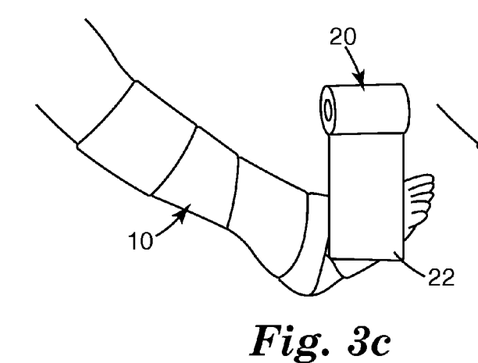
Figure 3D:
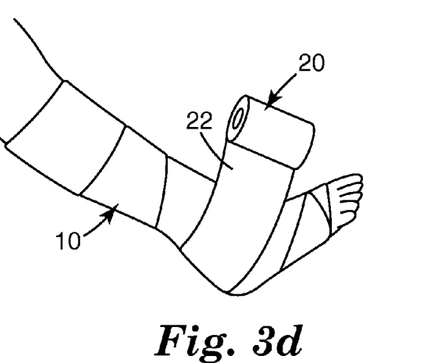
Figure 3E:
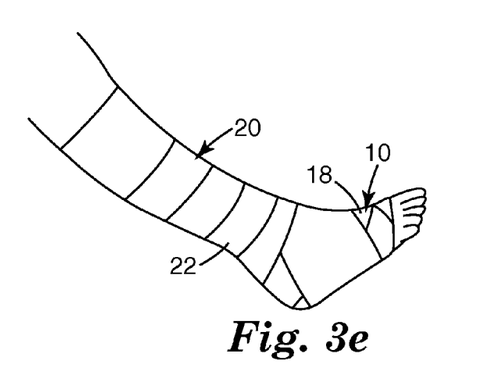

Referring to FIGS. 3a-3e, in preferred methods of using bandaging systems described herein, after any optional application of a non-elongated wound dressing or plaster to cover any open wound or wounds and the immediate skin area surrounding such wound(s), the inner bandage is applied with foam layer 12 facing towards and contacting the skin, typically in a spiral technique as exemplified in FIGS. 3a-3b with an appropriate overlap as detailed above. Preferably the inner bandage 10 is applied using a minimal of tension or no tension. If necessary or desired the inner bandage can be temporarily fixed, e.g., at the end of the last wrap, using a piece of adhesive tape or another type of suitable fastener. Alternatively but less preferable, a tab of adherent (preferably self adherent) material may be added on the inner skin-facing face and terminal end of the inner bandage in order to provide a suitable, integral fastening means for temporarily fastening the end of the last wrap of the inner bandage. Subsequently the outer bandage 20 is applied, again typically suitably in a spiral technique with an appropriate overlap (suitably a standard 50% overlap) as exemplified in FIGS. 3c-3e. Typically the outer bandage 20 is applied under tension, preferably near or at full extension. For patients who cannot tolerate the desired therapeutic compressive force due to pain or over-sensitivity, it may be necessary or desirable to apply the outer bandage 20 with a lower degree of extension. In applications over area of joints, e.g., over an ankle, a figure-of-eight configuration may be used in combination with a spiral technique to ensure complete coverage. Once in place, the outer bandage 20 advantageously holds the bandaging system in place for extended periods of time to provide a therapeutic effect.

Figure 4:
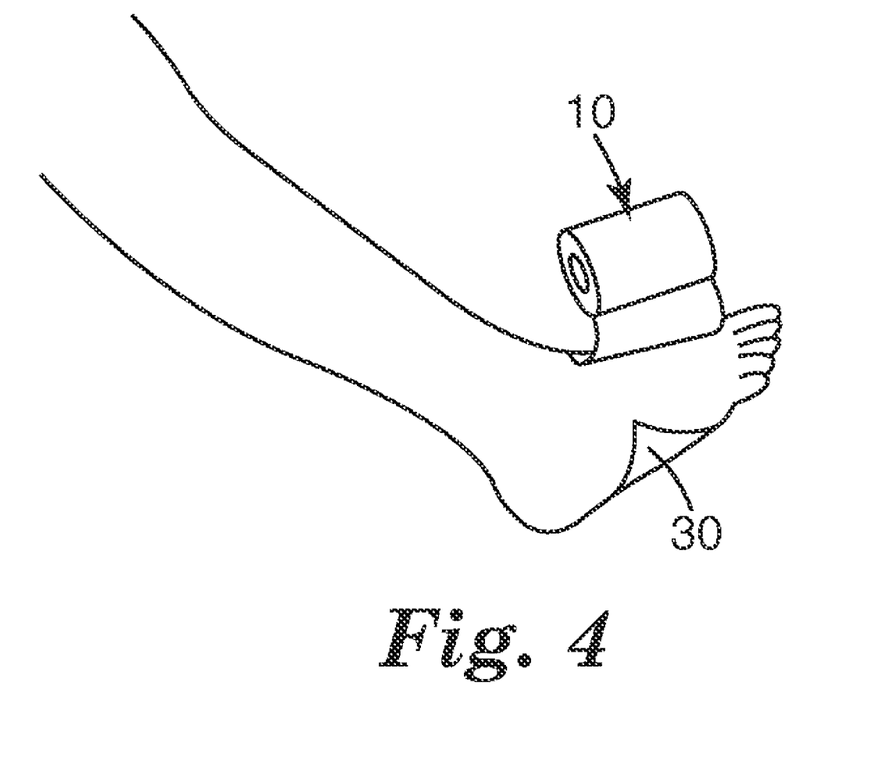

FIG. 4 illustrates an exemplary embodiment of the compression bandaging system wherein the system further includes non-elongated wound dressing 30 over which inner skin facing, elongated, elastic bandage 10 is applied.

The following examples further illustrate the practice of the present invention. The examples are not intended to limit the invention, which is defined in the appended claims.

TEST METHODS

Stretch and Recovery-of-Stretch Testing Procedure a. A stretch testing instrument consisting of the following is used: A frame with a fixed clamp at the top (upper clamp); a separate clamp (or other means) for attaching a weight to the bottom of the test specimen (lower clamp); a scale to measure the span of bench marks on the specimen graduated in units of 1 mm (¹⁄₂₄ inch) (or in units of percent of original gage length)±0.1% and a weight with an attached hook and a mass of 1000 g. The total tensioning weight including the weight having a mass of 1000 g and the lower clamp weighing 45 g is 1045 g.

b. Test specimen is allowed to condition at 23° C. and 50% relative humidity for 24 hours. Testing is performed at 23° C. and 50% relative humidity.

c. After conditioning, the test specimen is placed on a smooth flat surface and allowed to relax for at least 2 minutes. Thereafter a test sample dimension of 50.8 by 304.8 mm (2 by 12 inches) with the long direction parallel to test direction is prepared, e.g., by punching using a cutting template. (In particular, a template consisting of protruding cutting knives embedded in a wooden housing of about 290 mm×90 mm×17 mm dimension was used for cutting the test specimens to the required test sample dimension of 50.8 mm×304.8 mm. The template was placed in alignment on top of a conditioned, fully relaxed test specimen with the protruding knives facing the test specimen, and the test sample was cut by applying pressure (typically manually using a hammer) against the protruding knives opposing smooth wooden surface.)

d. After allowing the test sample to relax for at least 2 minutes, two bench marks of 127±1 mm (5 inch) apart are placed from the center of the test sample.

e. The two transverse ends of the test sample are then folded over until their outer edges are in line with the two bench marks. (By doing this, the ends of the test sample are reinforced and the long dimension is reduced from 304.8 mm (12 inches) down to 215.9 mm (8.5 inches) in length.)

f. One (transverse) end of the test specimen is then clamped with the upper clamp to the frame such that the test sample hangs freely and such that the lower edge of the clamp is in exact alignment with the upper bench mark.

g. On the lower (transverse) end of the test sample and in vertical alignment to the upper clamp, the lower clamp is attached, such that the upper edge of the clamp is in exact alignment with the lower bench mark. Accordingly the original test length (OL) is the distance between the two bench marks, 127 mm. Directly thereafter, the attachment hook of the 1000 g weight is inserted in an opening of the lower clamp, and then slowly (over approximately 5 s) the weight is allowed to hang freely thereby exerting tension to the test sample.

h. Using the scale, the distance between the bench marks is measured to the nearest 0.5 mm (or to the nearest 1% of original gage length), after the freely suspending the weight for 60±2 sec. The measured distance is the stretch length SL.

i. Directly thereafter, the weight and lower clamp are removed and the test sample is allowed to recover without tension.

j. Using the scale, the distance between the bench marks is measured to the nearest 0.5 mm (or to the nearest 1% of original gage length), after the tension has been removed for 120±4 sec. The measured distance is the recovery length RL.

k. Percent Stretch and Percent Recovery-of-Stretch are calculated as follows:

$$\% \text{ Stretch}=100\times(SL-OL)/OL$$

$$\% \text{ Recovery-of-Stretch}=100\times(SL-RL)/(SL-OL)$$

l. 6 test samples are tested for each test specimen and the mean values for % stretch and % recovery-of-stretch are calculated.

Water Vapor Transmission Rate (WVTR)

WVTR is measured in accordance with ASTM E 398-03 using a Water Permeability Tester L80-5000 (available from Lyssy AG, 8702 Zollikon, Switzerland), wherein the conditions of the wet (high humidity) chamber are 37.8° C. and 100% relative humidity and the conditions of the dry (low humidity) chamber are 37.8° C. and 10% relative humidity.

For measurements of inner bandage samples, the foam layer faced the wet (high humidity) chamber while then the elastic substrate was facing the opposing dry (low humidity) chamber.

If a material to be tested has any bias from one face to the other face, the face of the material that is to be facing towards the skin of the patient should be oriented towards the wet chamber.

Saline Absorbency Test a. A dry 5.1 cm by 5.1 cm sample (2 inch by 2 inch) is weighed to obtain dry weight (DW).

b. Directly thereafter, the sample is immersed in phosphate-buffered saline (Sigma-Aldrich Chemical Co., Milwaukee, Wis.; dry powder blend dissolved in water to 0.9% NaCl) for thirty minutes at 37° C.

c. Upon removal, the sample is allowed to drip freely for thirty seconds, and re-weighed to obtain wet weight (WW).

d. Percent absorbency of the sample is determined using the formula:

$$\% \text{ Absorbency}=((WW-DW)/(DW))\times100.$$

e. Three replications are performed with the reported result being the mean value.

Saline Swelling Test a. The width (dW), length (dL), and thickness (dT) of an approximate 5.1 cm by 5.1 cm (2 inches by 2 inches) dry sample are measured using a scale graduated in units of 0.5 mm (1/48 inch).

b. Directly thereafter, the sample is immersed in phosphate-buffered saline (Sigma-Aldrich Chemical Co., Milwaukee, Wis.; dry powder blend dissolved in water to 0.9% NaCl) for thirty minutes at 37° C.

c. Upon removal, the sample is allowed to drip freely for thirty seconds, and all three dimensions of the sample were immediately re-measured to obtain "wet" width (wW), length (wL) and thickness (wT).

d. Percent swelling of the sample is determined using the formula:

$$\% \text{ Swelling}=[((wW*wL*wT)-(dW*dL*dT))/(dW*dL*dT)]\times100.$$

e. Three replications are performed with the reported result being the mean value.

Sub-Bandage Pressure Measurement

Sub-bandage pressure is monitored using three pressure transducers taped to the skin of a leg of a healthy person (at rest and walking) under the applied compression bandage system. The procedure is based on the procedure described by Melhuish et al, in "Evaluation of Compression under an Elastic Tubular Bandage Utilised as an Introduction to Compression Therapy in the Treatment of Venous Leg Ulcers" Phlebology (2000) 15: 53-59.

a. Three strain gauge temperature-compensated (15-40° C.) pressure transducers, each having a diameter of 13 mm and a thickness of 3 mm (available by Gaeltec Ltd., Dunvegan, Isle of Skye, Scotland IV55 8GU) are used.

b. Before measurement, instrumentation is allowed a settling time of at least 5 minutes, and the pressure transducers are calibrated in an air chamber against a sphygmomanometer (available by Gaeltec Ltd., Dunvegan, Isle of Skye, Scotland IV55 8GU).

c. The transducers (typically connected via amplifiers and filters to a computer for data storage and analysis) are then placed on the lateral aspect of the non-dominant leg (of the test person) in line with the medial malleolus positioned as follows:

Sensor 1: at 8 cm above the lateral malleolus (i.e. approximately at the origin of the Achilles tendon);

Sensor 3: at 5 cm below the caput fibulae; and

Sensor 2: at a position located exactly at the midpoint between the positions Sensors 1 and 3. The sensors are fixed into positioned by taping down their connecting wires with one or two small pieces of tape; the transducer itself is not covered with tape.

d. The compression bandage system is applied (typically by an experienced nurse).

e. For measurement of sub-bandage resting pressures—pressure measurements are taken over a 5-minute period (typically with 20 measurement readings per second) with the test person sitting in an upright position with his legs extending horizontally and being supported from underneath. From this measurement set, a selection of a set of consecutive, steady (i.e., no statistically significant step changes in measured pressure readings) pressure readings over a period of at least one minute is made, and the mean value of said pressure readings is determined and reported in mm Hg. (The aforesaid selection is made to exclude significant changes in pressure readings resulting e.g., from movement of the test person. If no set of consecutive, relatively steady pressure readings over a period of at least one minute is observed, the measurement is repeated.)

f. For measurement of sub-bandage walking pressures—pressure measurements are taken over a 5-minute period (typically with 20 measurement readings per second) with the test person walking on a treadmill at no incline and at a velocity of 2.5 km/h. From this measurement set, a selection of a set of consecutive, steady (i.e., no statistically significant step changes in measured pressure readings) pressure readings over a period of at least one minute is made, and the mean value of said pressure readings is determined and reported in mm Hg. (The aforesaid selection is made to exclude statistically significant step changes in pressure measurement resulting e.g., from changes in walking speed, stumbling, etc. of the test person. If no set of consecutive, steady pressure readings over a period of at least one minute is observed, the measurement is repeated.)

Slippage Measurement

After a compression bandage system is applied to the leg of a healthy test person, a marker line is placed directly above the upper edge of the applied compression bandage system. Downward slippage (DS) is then determined, as the difference (measured by means of a scale graduated in units of 1 mm (±0.1%)) between the height of the upper edge of initially applied bandage system (initial height IH) and the height of the upper edge of the applied bandage system after 24 h of wear (height afterwards HA), DS=IH−HA. Results are reported in cm.

EXAMPLES

Preparation of Self-Adhering Compression Bandages for Use as an Outer Bandage

Self-adhering elastomeric bandages that do not adhere to clothing, hair or skin were prepared according to the process described in U.S. Pat. No. 4,984,584. In particular two thin dry-laid acrylic-binder-bonded nonwoven PET (1.5 denier) fibrous webs, each having a basis weight of 11 g/m$^2$, were brought into contact with 560 denier Spandex elastic yarns, longitudinally aligned and spaced apart (either 10, 14 or 20 epi) and partially extended (the draw ratio (ratio of stretched length to relaxed length of yarn) being selected to be either about 1.5:1 or 1.75:1) to provide a composite construction with the yarns between the two nonwoven webs, which was subsequently impregnated (coating weights between 31 and 52 g/m$^2$) with a latex based fluid binder mixture including 69% (based on fluid weight) of an aqueous anionic colloidal dispersion of 2,3 dichloro-1,3-butadiene and chloroprene copolymer (about 50% solids, 40% chlorine, Brookfield viscosity (spindle 1, 6 & 30 rpm) at 25° C. 10 cps) and 31% (based on fluid weight) of an aqueous dispersion of aromatic modified hydrocarbon resin having a ring and ball softening point of about 70° C. (about 55% solids, Brookfield viscosity at 25° C. 1,000 cps) plus relative to 100 parts of copolymer 4 parts of zinc oxide, 2 parts antioxidant, 0.5 parts pigment and 0.16 parts of a defoamer. After drying, the resulting sheet material was slit into bandages 10 cm wide and between 2 to 2.5 meters long (unstretched dimensions).

The following table summarized the prepared self-adhering compression bandages for use as outer bandages:

TABLE 1

| Designation | epi | Draw ratio | Coating weight (g/m$^2$) | Relaxed basis weight (g/m$^2$) | % Stretch* | % Recovery* | WVTR (g/m$^2$/24 h) |
|---|---|---|---|---|---|---|---|
| O1 | 10 | ~1.5:1 | 31 | 130 | 50 | 98 | 3470 |
| O2 | 14 | ~1.5:1 | 45 | 140 | 37 | 98 | 3608 |
| O3 | 14 | ~1.75:1 | 52 | 162 | 52 | 97 | — |
| O4 | 20 | ~1.75:1 | 45 | 173 | 55 | 98 | — |

*in the longitudial direction

Preparation of Elastic Substrate/Foam Laminates for Use as an Inner Bandage

As elastic substrate, in each case, a self-adherent elastomeric web material (having dimensions of 10 cm by 2 m) that does not adhere to clothing, hair or skin was used. Similar to the outer bandage, the sheet material for the elastic substrate was prepared according to the process described in U.S. Pat. No. 4,984,584 using 280 denier Spandex yarns at 10 epi between two nonwoven webs as described above with a draw ratio of about 3.5:1 and impregnating (coating weight of 52 g/m$^2$) with a latex based fluid binder mixture as described above. After drying, the resulting sheet material (having a relaxed basis weight of 179 g/m$^2$) was slit into strips of 10 cm wide and 2 meters long (unstretched dimensions) for use as elastic substrate. The elastic substrate showed a stretch capability in the longitudinal direction of 110% and a recovery-of-stretch capability in the longitudinal direction of 98%; and is referred to in the following as ES.

Four different polyurethane foams were used as follows:

A hydrophobic polyurethane foam available from THE WOODBRIDGE GROUP (Mississauga, Ontario, Canada) under the trade designation BIOFREE SM 25; referred to in the following as F1. F1 had a thickness of 4 mm, a measured saline absorbency of 2969% and a saline swelling of 0.4%.

A hydrophobic polyurethane foam having hydrophilic characteristics available from Fulflex, Inc (Middelton, R.I., USA) under trade designation POLYCRIL 400; referred to in the following as F2. F2 had a thickness of 4 mm, a measured saline absorbency of 1089% and a saline swelling of 8%.

A hydrophilic polyurethane foam available from Fulflex, Inc (Middelton, R.I., USA) under trade designation POLYCRIL 300; referred to in the following as F3. F3 had a thickness of 3 mm, a measured saline absorbency of 560% and a saline swelling of 8%.

A hydrophilic polyurethane foam available from Corpura B.V. (Etten-Leur, Netherlands) under the trade designation VIVO MFC.03; referred to in the following as F4. F4 had a thickness of 3 mm, a measured saline absorbency of 1805% and a saline swelling of 26%.

In manually preparing the foam-elastic substrate laminates, acrylic adhesive based transfer adhesive strips (thickness 76.2 m, width of 16 and/or 28 cm) were applied extending lengthwise across the width (starting from the two longitudinal edges working towards the center) of a face of elongated foam layer sheet having outer dimensions of 31 to 49 cm by 2 to 2.5 m for F1 to F4. Slight pressure was applied by hand, establishing a first contact between adhesive and foam, and to further enhance good contact, the transfer adhesive was then manually rolled-over with a rubber hand roller over its release liner, rolling two to three times over the entire length and width of the foam-adhesive composite. After removing the release liner of the foam-adhesive composite, a face of a relaxed elastic substrate (dimensions 10 cm by 2 m) was placed over the exposed face of the transfer adhesive. Depending on the particular width of the foam layer sheet, this step was repeated with two or three additional relaxed elastic substrates. (Previous to step of application to the adhesive, each elastic substrate was placed flat on a smooth surface and allowed to relax completely for at least 2 minutes.) To ensure good contact between the elastic substrate(s) and the adhesive, the composite was turned over and the foam side was manually rolled-over with a rubber hand roller. The resulting composite was cut to width and in length by removing around 5 mm at both transverse ends (both relative to the width and length of the elastic substrate(s)) to yield inner bandages having relaxed dimensions of 10 cm and around 1.9 m, with the foam layer being co-extensive with the elastic substrate. The bandages were then wound on cores having an inner diameter of 30 mm for later use as inner bandage.

The following table summarized the prepared elastic substrate/foam laminates:

TABLE 2

| Designation | WVTR (g/m²/24 h) | % Stretch* | % Recovery* |
|---|---|---|---|
| ES-F1 | 740 | 39 | 97 |
| ES-F2 | 799 | 45 | 96 |
| ES-F3 | 401 | 38 | 96 |
| ES-F4 | 806 | 69 | 98 |

*in the longitudinal direction

Exemplary Compression Bandaging Systems

Exemplary bandaging systems using outer bandages (Table 1) in conjunction with inner bandages (Table 2) as listed in the following table were used in testing (summarized below) on legs of healthy, in house volunteers.

TABLE 3

| Example No. | Outer Bandage | Inner Bandage |
|---|---|---|
| 1 | O1 | ES-F2 |
| 2 | O2 | ES-F2 |
| 3 | O3 | ES-F2 |
| 4 | O4 | ES-F2 |
| 5 | O2 | ES-F1 |
| 6 | O2 | ES-F3 |
| 7 | O2 | ES-F4 |
| C1 | 4 layer compression wrap | |

Also a four layer compression bandage commercially available under the trade designation PROFORE (18-25 cm ankle pack) from Smith & Nephew Medical Ltd. (Hull HU3 2BN, England) was used as a comparative example, C1. This bandage consists of an inner layer of orthopedic wool (a polyester-based "wool"), a second layer crepe bandage, a third layer of light compression bandage and a fourth layer of self-adherent flexible bandage.

Method of Applying Exemplary Compression Bandaging Systems

The inner bandage with foam layer facing towards and contacting the skin was wound onto the lower leg without any tension in a simple (ascending) spiral technique using about a 10% overlap, starting at the base of the toes and ending just below the fibular head. After cutting any excess bandage length, the applied inner bandage was then temporarily secured at the end of the last wrap with a small piece of medical tape, such as 3M MICROPORE (available by 3M Company, St. Paul, USA). Subsequently, the outer bandage was applied at full stretch starting at the base of the toes using two spiral turns to secure the bandage and then two figure-of-eight turns around the ankle joint (to ensure the heel was completely covered). Application was continued then in a simple (ascending) spiral technique with a 50% overlap ending just below the fibular head and if necessary cutting off any excess length of the bandage.

Method of Applying Comparative Four Layer Compression Bandage

Application was carried out in accordance with the instruction of manufacturer. First the inner layer was applied from the base of the toes to the knee using a simple (ascending) spiral technique with 50% overlap. Any excess material was cut off and the end was secured with a piece of tape. In the next step, the second layer was applied from the base of the toes to the knee over the inner bandage (a slight border of the inner layer was allowed to remain visible) using a simple spiral technique, applying at mid-stretch and 50% overlap. Any excess material was cut off and the end of the second layer was secured with piece of tape. The third layer was then applied, starting at the base of the toes up to the knee, using a figure-of-eight technique at 50% extension of the bandage. The end of the bandage was then secured with a piece of tape. Then the fourth layer was applied starting from the toes to the knee using a spiral technique with 50% overlap and 50% extension. Following the application of the fourth layer, the cohesive bandage, the surface was lightly pressed by hand to ensure sufficient cohesion of the bandage to itself.

For all testing, all bandages were applied by an experienced nurse.

After application, the exemplary bandaging systems in accordance with the invention described herein are considerably thinner than that observed for the comparative bandaging system. The comparative bandage system had an applied thickness of 6.03 mm, while for example the bandaging system of Examples 2, 5 and 7 had an applied thickness of 2.90, 1.87 and 3.25 mm, respectively (as measured using a digital slide gauge (available by Preisser Messtechnik GmbH & Co. KG, 72501 Gammertingen, Germany). Also advantageously, the exemplary bandaging systems in accordance with the invention described herein have an applied thickness considerably thinner than the sum of the thicknesses of their individual outer and inner bandages. For example, in the bandaging system of Example 2 including an outer bandage (O1) having a thickness of 0.89 mm and an inner bandage (ES-F2) having a thickness of 5.38 mm, the applied thickness was 2.90 mm.

First Series of Sub-Bandage Pressure Testing

Four sets of 12 in-house, healthy volunteers were used for four sets of comparative testing of sub-bandage pressure. Compression bandaging systems of Examples 1 to 4 were each compared to comparative C1. In all testing—measuring pressures at rest and during walking in accordance to the sub-bandage pressure measurement procedure detailed above—the compression bandage system was applied to the non-dominant leg of the volunteer. The same volunteer was used with the testing of one of Examples 1 to 4 and in each case C1 in sequence. After testing one system, it was removed, leaving the three pressure transducers untouched in their secured positions. The pressure transducers were re-zeroed appropriately. The second bandage was applied and pressure measurements were made. The means for the sub-bandage pressure measurement results for all 12 volunteers were computed and are reported in Table 4.

TABLE 4

| Example No. | Sensor 1 Rest (mm Hg) | Sensor 2 Rest (mm Hg) | Sensor 3 Rest (mmHg) | Sensor 1 Walk (mm Hg) | Sensor 2 Walk (mm Hg) | Sensor 3 Walk (mm Hg) |
|---|---|---|---|---|---|---|
| 1 | 67.00 | 31.75 | 32.00 | 65.50 | 37.25 | 33.50 |
| C1 | 57.75 | 36.50 | 35.75 | 59.00 | 40.25 | 35.00 |
| 2 | 67.75 | 41.00 | 37.50 | 64.25 | 37.00 | 36.50 |

TABLE 4-continued

| Example No. | Sensor 1 Rest (mm Hg) | Sensor 2 Rest (mm Hg) | Sensor 3 Rest (mmHg) | Sensor 1 Walk (mm Hg) | Sensor 2 Walk (mm Hg) | Sensor 3 Walk (mm Hg) |
|---|---|---|---|---|---|---|
| C1 | 50.00 | 37.50 | 36.50 | 52.50 | 33.50 | 37.50 |
| 3 | 53.75 | 39.25 | 31.75 | 57.00 | 41.50 | 33.00 |
| C1 | 47.00 | 37.50 | 30.25 | 48.50 | 42.50 | 36.00 |
| 4 | 50.25 | 44.25 | 26.75 | 57.00 | 42.75 | 27.00 |
| C1 | 44.25 | 38.50 | 27.75 | 45.00 | 37.25 | 28.50 |

Second Series of Sub-Bandage Pressure Testing

One set of 12 in-house, healthy volunteers were used for comparative testing of sub-bandage pressure of compression bandaging systems of Examples 2, 5, 6 and comparative C1 in sequence. As in the first series of sub-bandage pressure testing, the compression bandage system was applied to the non-dominant leg of the volunteer. As in the previous testing, the first system was applied, tested, removed leaving the pressure transducers untouched in their in their secured positions, transducers re-zeroed, next system applied, tested, removed, etc. until the fourth system was applied and tested. The mean for the sub-bandage pressure measurement results for all 12 volunteers were computed and are reported in Table 5.

TABLE 5

| Example No. | Sensor 1 Rest (mm Hg) | Sensor 2 Rest (mm Hg) | Sensor 3 Rest (mm Hg) | Sensor 1 Walk (mm Hg) | Sensor 2 Walk (mm Hg) | Sensor 3 Walk (mm Hg) |
|---|---|---|---|---|---|---|
| 2 | 43.75 | 49.50 | 24.91 | 46.17 | 56.50 | 29.58 |
| 5 | 46.91 | 51.67 | 31.83 | 48.0 | 57.33 | 37.50 |
| 6 | 51.33 | 61.33 | 36.83 | 55.92 | 69.58 | 42.58 |
| C1 | 51.08 | 49.17 | 31.25 | 54.17 | 55.67 | 39.50 |

Slippage Measurements of Compression Bandage Systems

Four sets of 12 in-house, healthy volunteers were used for four sets of comparative testing of downward slippage after 24 h of wearing applied bandage. Compression bandaging systems of Example 5, 6, 7 and C1 were compared in each case to compression bandaging system of Example 2. In order to provide a direct comparison, the bandage system of Example 2 was applied to one leg of the volunteer, and the second bandage system, Examples 5, 6, 7 or C1 respectively, was applied to the other leg. The mean for the slippage results for all 12 volunteers were computed and are reported in Table 6.

TABLE 6

| Example No. | Slippage after 24 h wear (cm) |
|---|---|
| 2 | 0.32 |
| 5 | 0.41 |
| 2 | 0.34 |
| 6 | 0.50 |
| 2 | 0.48 |
| 7 | 0.81 |
| 2 | 0.38 |
| C1 | 4.18 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A compression bandaging system comprising:
   a) an inner skin facing, elongated, elastic bandage comprising:
      (i) an elongated, elastic substrate, and
      (ii) an elongated foam layer affixed to a face of the substrate and extending 33% or more across the face of the substrate in transverse direction and 67% or more across the face of the substrate in longitudinal direction; and
   b) an outer, elongated, self-adhering elastic bandage configured to hold the bandaging system in place, the outer bandage having a compressive force when extended;
   wherein in use, the inner skin facing, elongated, elastic bandage adheres to the outer, elongated, self-adhering elastic bandage under elastic extension without the use of a fastening mechanism and wherein the bandaging system is free of any additional elongated bandages.

2. The compression bandaging system of claim 1, wherein in use, the foam layer of the inner bandage faces the skin and the outer bandage overlies the inner bandage.

3. The compression bandaging system of claim 1, wherein the inner skin facing, elongated, elastic bandage adheres to the outer, elongated, self-adhering elastic bandage.

4. The compression bandaging system of claim 1, the elongated, elastic substrate having an outer face not affixed to the foam layer, wherein the outer face comprises a self-adhering material.

5. The compression bandaging system of claim 4, wherein the self-adhering material comprises a self-adhering elastomeric material.

6. The compression bandaging system of claim 1, wherein the inner skin facing, elongated, elastic bandage provides less compression than the outer, elongated, self-adhering elastic bandage when extended.

7. The compression bandaging system of claim 1, wherein the elongated foam layer is coextensive with the elongated, elastic substrate.

8. The compression bandaging system of claim 1, further comprising a non-elongated wound dressing or plaster.

9. The compression bandaging system of claim 1, wherein the outer bandage has a stretch capability of 75% at most in the longitudinal direction.

10. The compression bandaging system of claim 1, wherein
the outer bandage has a recovery-of-stretch capability of at least 85% in the longitudinal direction.

11. The compression bandaging system of claim 1, wherein
the inner bandage has a stretch capability of less than 75% in the longitudinal direction.

12. The compression bandaging system of claim 1, wherein
the inner bandage has a recovery-of-stretch capability of at least 80% in the longitudinal direction.

13. The compression bandaging system of claim 1, wherein
the foam layer has a thickness greater than 1.6 mm.

14. A compression bandage kit comprising:
a) an inner skin facing, elongated, elastic bandage comprising:
  (i) an elongated, elastic substrate comprising first and second faces, the second face comprising a self-adhering material; and
  (ii) an elongated layer of foam comprising a face affixed to the first face of the substrate and an outer exposed face not affixed to the substrate wherein the elongated layer of foam extends 33% or more across the first face of the substrate in transverse direction and 67% or more across the first face of the substrate in longitudinal direction; and
b) an outer, elongated, self-adhering elastic bandage configured to hold the bandaging system in place, the outer bandage having a compressive force when extended;
wherein, in use, the outer exposed face of the foam layer faces the skin and the outer bandage overlies the inner bandage, wherein the inner and outer bandages are configured and adapted such that in use the bandages remain adhered to one another under elastic extension without the use of a fastening mechanism, and wherein the bandaging kit is free of any additional elongated bandages.

* * * * *

UNITED STATES PATENT AND TRADEMARK OFFICE
CERTIFICATE OF CORRECTION

PATENT NO. : 8,403,873 B2
APPLICATION NO. : 12/945019
DATED : March 26, 2013
INVENTOR(S) : Jan Schuren It is certified that error appears in the above-identified patent and that said Letters Patent is hereby corrected as shown below:

Title Page, Col. 1 Item [75] (Inventors)
Line 6            Delete "Sudiohn" and insert -- Sudlohn --, therefor.

Title Page 2, Col. 2, Item [56] (Other Publications)
Line 7            Delete "Ahesives)." and insert -- Adhesives). --, therefor.

In the Specifications:

Column 6
Line 45           Delete "(Lohman" and insert -- (Lohmann --, therefor.

Column 9
Line 12           After "above" insert -- . --, therefor.

Column 10
Line 56           Delete "sytrene" and insert -- styrene --, therefor.

Column 15, Table 1
Line 66           Delete "longitudial" and insert -- longitudinal --, therefor.

Column 16
Line 26           Delete "(Middelton," and insert -- (Middletown, --, therefor.
Line 31           Delete "(Middelton," and insert -- (Middletown, --, therefor.

In the Claims:

Column 20
Line 48           In Claim 4, after "claim 1," insert -- wherein --, therefor.

Signed and Sealed this
Twenty-third Day of July, 2013

Teresa Stanek Rea
*Acting Director of the United States Patent and Trademark Office*